(12) United States Patent
Kozloski et al.

(10) Patent No.: US 11,776,688 B2
(45) Date of Patent: Oct. 3, 2023

(54) CAPTURING USER CONSTRUCTED MAP OF BODILY REGION OF INTEREST FOR REMOTE TELEMEDICINE NAVIGATION

(71) Applicant: International Business Machines Corporation, Armonk, NY (US)

(72) Inventors: James R. Kozloski, New Fairfield, CT (US); Roger D. Traub, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 456 days.

(21) Appl. No.: 17/098,810

(22) Filed: Nov. 16, 2020

(65) Prior Publication Data
US 2022/0157450 A1 May 19, 2022

(51) Int. Cl.
*G16H 40/67* (2018.01)
*G06T 7/00* (2017.01)
(Continued)

(52) U.S. Cl.
CPC ........... *G16H 40/67* (2018.01); *A61B 5/0013* (2013.01); *A61B 5/0022* (2013.01);
(Continued)

(58) Field of Classification Search
None
See application file for complete search history.

(56) References Cited

U.S. PATENT DOCUMENTS

| 6,544,198 | B2 | 4/2003 | Chong et al. |
| 6,575,904 | B2 | 6/2003 | Nagai et al. |

(Continued)

FOREIGN PATENT DOCUMENTS

| CN | 201491168 U | 5/2010 |
| JP | 2015091432 A | 5/2015 |

(Continued)

OTHER PUBLICATIONS

Author Unknown, "WI—Challenge Medical Imaging Using Grid Computing and Mobile Device Displays," An IP.com Prior Art Database Technical Disclosure, Original Publication Date: Apr. 27, 2009: IP.com No. IPCOM000182347D (Apr. 27, 2009); 4 pages.

(Continued)

*Primary Examiner* — Rodney E Fuller
(74) *Attorney, Agent, or Firm* — Cantor Colburn LLP; Kristofer Haggerty

(57) ABSTRACT

A computer-implemented method for capturing a user constructed map of bodily region of interest for remote telemedicine navigation includes receiving, by a user-device, a request for capturing data for constructing a model of the bodily region using a designated capture-device. The method further includes generating, by the user-device, a visual feedback for capturing the data. Generating the visual feedback includes displaying a representation of the bodily region, and modulating, in response to the capture-device scanning the bodily region, the representation with a first indicator that indicates a duration to maintain a position of the capture-device. Generating the visual feedback includes further modulating, in response to completion of scanning the bodily region, the representation with a second indicator that indicates completion of the scan. The method further includes constructing, by the user-device, the model of the bodily region using data that is acquired by the capture-device by scanning the bodily region.

25 Claims, 7 Drawing Sheets

(51) Int. Cl.
*G06T 7/11* (2017.01)
*G16H 50/50* (2018.01)
*G16H 30/20* (2018.01)
*G16H 30/40* (2018.01)
*A61B 5/00* (2006.01)
*H04N 23/60* (2023.01)
*G16H 80/00* (2018.01)

(52) U.S. Cl.
CPC ............ *A61B 5/0064* (2013.01); *A61B 5/743* (2013.01); *A61B 5/7465* (2013.01); *G06T 7/0012* (2013.01); *G06T 7/11* (2017.01); *G16H 30/20* (2018.01); *G16H 30/40* (2018.01); *G16H 50/50* (2018.01); *H04N 23/64* (2023.01); *G06T 2200/24* (2013.01); *G06T 2207/30168* (2013.01); *G16H 80/00* (2018.01)

(56) References Cited

U.S. PATENT DOCUMENTS

| | | | |
|---|---|---|---|
| 7,835,926 B1* | 11/2010 | Naidoo | G16Z 99/00 |
| | | | 705/2 |
| 8,827,920 B2 | 9/2014 | Lee et al. | |
| 8,953,837 B2* | 2/2015 | Gilad-Gilor | A61B 5/742 |
| | | | 382/128 |
| 9,717,412 B2 | 8/2017 | Roham et al. | |
| 10,143,373 B2* | 12/2018 | Gilad-Gilor | G16H 40/63 |
| 10,660,607 B2* | 5/2020 | Ryu | A61B 8/465 |
| 2017/0011179 A1 | 1/2017 | Arshad et al. | |
| 2017/0164930 A1 | 6/2017 | Oh et al. | |
| 2017/0296059 A1 | 10/2017 | Anderson | |
| 2019/0320900 A1 | 10/2019 | Majmudar | |
| 2020/0383582 A1* | 12/2020 | Bychkov | A61B 5/7282 |
| 2021/0134458 A1* | 5/2021 | Mason | G16H 40/67 |
| 2021/0369115 A1* | 12/2021 | Zatvan | A61B 5/1032 |

FOREIGN PATENT DOCUMENTS

RU 2642913 C2 1/2018
WO 2015192121 A1 12/2015

OTHER PUBLICATIONS

3M, "Hear It. As if you Were There." 3M Littmann TeleSteth System Brochure, 2012, 8 pages.

Capritto, "4 Ways to Check for Skin Cancel with Your Smartphone," CNET Health and Wellness, Jan. 1, 2020, 7 pages.

Filippeschi et al., "A novel Diagnostician Haptic Interface for Tele-palpation," Proceedings of the 27th IEEE International Symposium on Robot and Human Interactive Communication, Aug. 27-31, 2018, pp. 328-335.

* cited by examiner

CAPTURING USER CONSTRUCTED MAP OF BODILY REGION OF INTEREST FOR REMOTE TELEMEDICINE NAVIGATION

BACKGROUND

The present invention generally relates to programmable computers, and more specifically, to programmable computers configured to capture a user constructed map of bodily region of interest for remote telemedicine navigation. The present invention further relates to using the programmable computer to provide feedback to the user through a visual representation of the quality or the samples being taken so as to allow user to intuitively go back and resample poorly covered regions, until a full construction is made.

Various technological advances have fostered the development of various telemedicine capabilities. Improvements in telemedicine capabilities may increase adoption of telemedicine by healthcare-professionals and patients. Telemedicine can include an online experience in which a healthcare-professional, such as a doctor, a nurse, or any other such personnel and a patient are simultaneously online and in consultation with each other. In such an online session, the healthcare-professional can guide the patient, and in some case, remotely capture one or more health metrics of the patient.

SUMMARY

One or more embodiments of the present invention includes a computer-implemented method for capturing a user constructed map of bodily region of interest for remote telemedicine navigation. The computer-implemented method includes receiving, by a user-device, a request for capturing data for constructing a model of the bodily region using a designated capture-device. The method further includes generating, by the user-device, a visual feedback for capturing the data. Generating the visual feedback includes displaying a representation of the bodily region. Generating the visual feedback further includes modulating, in response to the capture-device scanning the bodily region, the representation with a first indicator that indicates a duration to maintain a position of the capture-device. Generating the visual feedback includes further modulating, in response to completion of scanning the bodily region, the representation with a second indicator that indicates completion of the scan. The method further includes constructing, by the user-device, the model of the bodily region using data that is acquired by the capture-device by scanning the bodily region.

According to one or more embodiments of the present invention, modulating the representation comprises changing at least one from a group of parameters comprising color, contrast, brilliance, brightness, sharpness, texture rendering, distance cues, distortion, and skew of the representation.

According to one or more embodiments of the present invention, the method further includes transmitting the constructed model of the bodily region for visualization and interaction by a healthcare-professional.

According to one or more embodiments of the present invention, the method further includes encrypting the model of the bodily region prior to the transmitting.

In one or more embodiments of the present invention, the representation of the bodily region is divided into a plurality of portions, and each portion is captured separately by the capture-device.

In one or more embodiments of the present invention, determining completion of the scan by the capture-device includes comparing one or more quality parameters of the scan with respective quality thresholds.

According to one or more embodiments of the present invention, the quality thresholds are prescribed as part of the request for capturing data.

According to one or more embodiments of the present invention, a system includes a memory having computer readable instructions, and one or more processors for executing the computer readable instructions. The computer readable instructions control the one or more processors to perform operations for capturing user constructed map of bodily region of interest for remote telemedicine navigation. The operations include receiving a request for capturing data for constructing a model of the bodily region using a designated capture-device. The operations further include generating a visual feedback for capturing the data. Generating the visual feedback includes displaying a representation of the bodily region, and modulating, in response to the capture-device scanning the bodily region, the representation with a first indicator that indicates a duration to maintain a position of the capture-device. Generating the visual feedback includes further modulating, in response to completion of scanning the bodily region, the representation with a second indicator that indicates completion of the scan. The operations further include constructing the model of the bodily region using data that is acquired by the capture-device by scanning the bodily region.

According to one or more embodiments of the present invention, a computer program product includes a computer readable storage medium having program instructions embodied therewith. The program instructions are executable by one or more processors to cause the one or more processors to perform operations for capturing user constructed map of bodily region of interest for remote telemedicine navigation, The operations include receiving a request for capturing data for constructing a model of the bodily region using a designated capture-device. The operations further include generating a visual feedback for capturing the data. Generating the visual feedback includes displaying a representation of the bodily region, and modulating, in response to the capture-device scanning the bodily region, the representation with a first indicator that indicates a duration to maintain a position of the capture-device. Generating the visual feedback includes further modulating, in response to completion of scanning the bodily region, the representation with a second indicator that indicates completion of the scan. The operations further include constructing the model of the bodily region using data that is acquired by the capture-device by scanning the bodily region.

One or more embodiments of the present invention include a computer-implemented method for capturing user constructed map of bodily region of interest for remote telemedicine navigation. The computer-implemented method includes receiving, by a cloud-server, a request for capturing data for constructing a model of the bodily region of an identified user. The method further includes determining, by the cloud-server, a designated capture-device to be used by the identified user to capture the data for constructing the model. The method further includes transmitting, by the cloud-server, the request to a user-device associated with the user along with an identification of the designated capture-device. The method further includes providing, at runtime, by the cloud-server, a visual feedback for capturing the data. Generating the visual feedback includes causing the user-device to display a representation of the bodily region. Generating the visual feedback further includes modulating, in response to the capture-device scanning the bodily region, the representation with a first indicator that indicates a duration to maintain a position of the capture-device. Generating the visual feedback further includes further modulating, in response to completion of scanning the bodily region, the representation with a second indicator that indicates completion of the scan. The operations further include receiving, by the cloud-server, the data that is acquired by the capture-device, and constructing, by the cloud-server, the model of the bodily region using the data that is acquired by the capture-device by scanning the bodily region.

In one or more embodiments of the present invention, the operations further include transmitting the constructed model of the bodily region for visualization and interaction by a healthcare-professional.

According to one or more embodiments of the present invention, a system includes a memory having computer readable instructions, and one or more processors for executing the computer readable instructions. The computer readable instructions control the one or more processors to perform operations for capturing user constructed map of bodily region of interest for remote telemedicine navigation. The operations include receiving a request for capturing data for constructing a model of the bodily region of an identified user. The operations further include determining a designated capture-device to be used by the identified user to capture the data for constructing the model. The operations further include transmitting the request to a user-device associated with the user along with an identification of the designated capture-device. The operations further include providing, at runtime, a visual feedback for capturing the data. Generating the visual feedback includes causing the user-device to display a representation of the bodily region. Generating the visual feedback further includes modulating, in response to the capture-device scanning the bodily region, the representation with a first indicator that indicates a duration to maintain a position of the capture-device. Generating the visual feedback further includes further modulating, in response to completion of scanning the bodily region, the representation with a second indicator that indicates completion of the scan. The operations further include receiving the data that is acquired by the capture-device, and constructing the model of the bodily region using the data that is acquired by the capture-device by scanning the bodily region.

In one or more embodiments of the present invention, modulating the representation includes changing at least one from a group of parameters that includes color, contrast, brilliance, brightness, sharpness, texture rendering, distance cues, distortion, and skew of the representation.

In one or more embodiments of the present invention, the operations further include transmitting the constructed model of the bodily region for visualization and interaction by a healthcare-professional.

Embodiments of the present invention facilitate capturing user constructed map of bodily region of interest for remote telemedicine navigation. In one or more embodiments of the present invention, the user constructed map of the bodily region is captured in an "offline manner" or in an "asynchronous manner" i.e., the patient captures the bodily region at a first timepoint, and at a later time, a healthcare-professional views and navigates the captured data. To facilitate such asynchronous remote telemedicine, embodiments of the present invention facilitate, at the time of capturing the user, providing feedback to the patient, i.e., user that is capturing the data, through a visual representation of the quality of the samples being captured to allow the user to go back and resample/recapture one or more regions that have a quality level that is below a threshold value. Providing such a feedback can be continued until a full construction of the bodily region is made as per the quality thresholds that are configured.

Other embodiments of the present invention implement features of the above-described method in computer systems and computer program products.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

DETAILED DESCRIPTION

Figure 1:
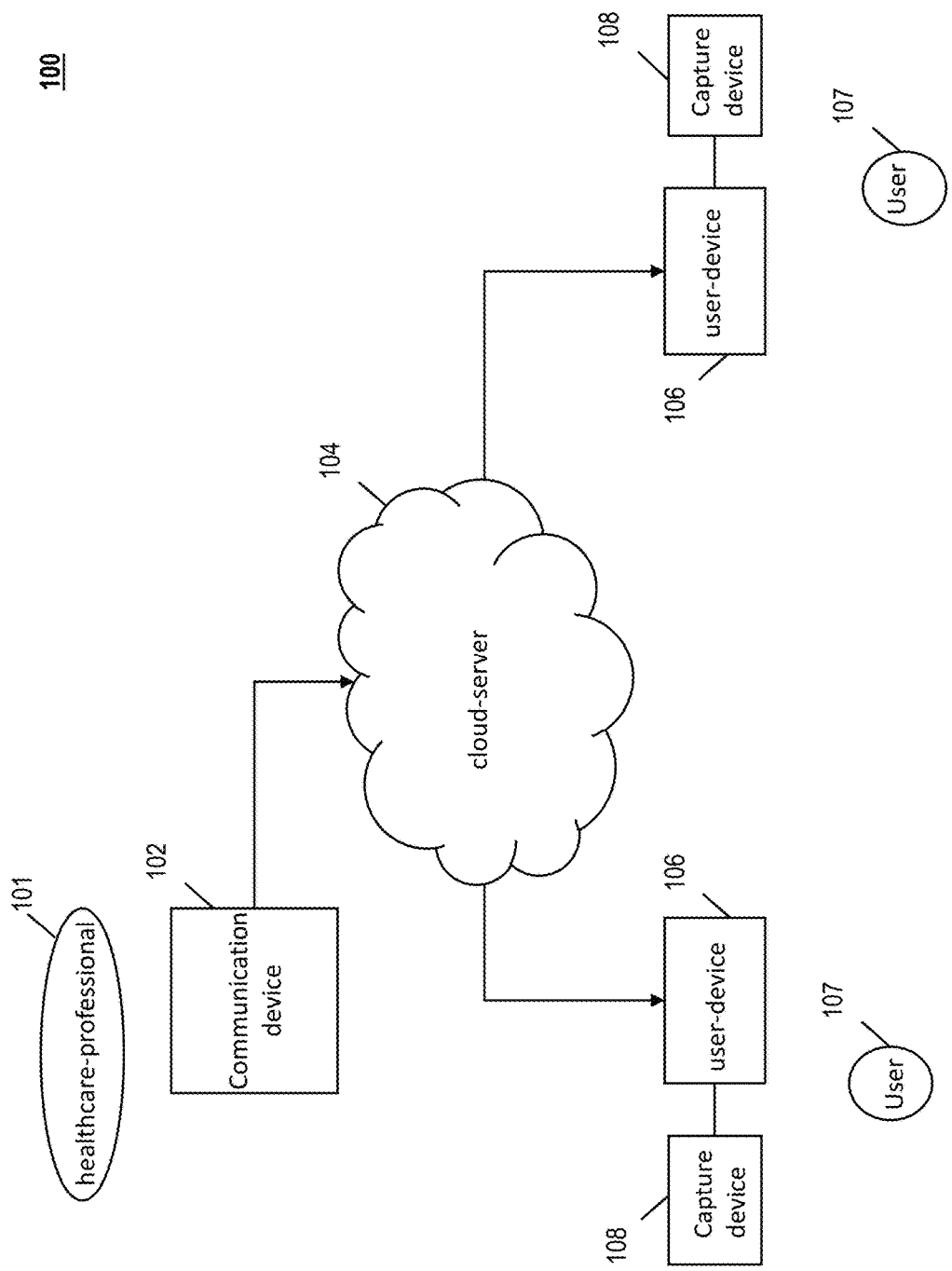
FIG. 1 is a block diagram of a system for capturing a user constructed map of a bodily region of interest for remote telemedicine navigation according to one or more embodiments of the present invention.

Embodiments of the present invention facilitate capturing user constructed map of bodily region of interest for remote telemedicine navigation. In one or more embodiments of the present invention, the user constructed map of the bodily region is captured in an "offline manner" or in an "asynchronous manner" i.e., the patient captures the bodily region at a first timepoint, and at a later time, a healthcare-professional views and navigates the captured data. To facilitate such asynchronous remote telemedicine, embodiments of the present invention facilitate, at the time of capturing the user, providing feedback to the patient, i.e., user that is capturing the data, through a visual representation of the quality of the samples being captured to allow the user to go back and resample/recapture one or more regions that have a quality level that is below a threshold value. Providing such a feedback can be continued until a full construction of the bodily region is made as per the quality thresholds that are configured.

Embodiments of the present invention further facilitate triggering collection of multiple samples of the bodily region and constructing a model of a user-centric view of the bodily region, and providing a visual indicator of the quality of the model being constructed by the current samples from the bodily region. The model is then shared with the healthcare-professional for a virtual examination of the bodily region. Embodiments of the present invention further facilitate encrypting the data at various stages to ensure privacy and security of the data that is captured and shared between the patient and the healthcare-professional.

Presently available solutions in telemedicine facilitate "synchronous" data capturing and sharing of models of bodily regions, where healthcare-professionals and a patient are simultaneously online, with the healthcare-professionals guiding the patient to capture the model. A need exists to separate 1) the remote collection of data from a patient's body part, 2) the viewing, navigation, and diagnosing of a patient using the recorded data, and 3) the healthcare-professional/patient meeting, in order to implement efficient and effective telemedicine solutions. Once separated, a healthcare-professional can request, remotely, that a body part scan be conducted by the patient, using the visual indication of the quality of scanning as described herein. Further, in one or more embodiments of the present invention, the recorded data is assembled into a virtual model, which functionally incorporates a navigation according to the healthcare-professional's use. The healthcare-professional can view and navigate the assembled model intuitively and asynchronously for diagnosis purposes, and a subsequent synchronous telemedicine meeting may be used for the patient and healthcare-professional to discuss this diagnosis and optionally navigate the data together.

Embodiments of the present invention address such technical challenges and deficiencies regarding asynchronous capture and navigation of the bodily region in the available solutions. In one or more embodiments of the present invention, data for a specific bodily region can be captured from patient body parts, using various sensory modalities, such as imaging, temperature, pressure, sound, haptic, and applying various analytical features thereof. Further, the patient multimodal data that is collected by the patient is mapped into an estimated coordinate system, wherein the patient is automatically guided to move the recording device in order to approximate and reconstruct a complete doctor-centric map of the patient's bodily region for the purpose of subsequent and arbitrary healthcare-professional navigation, in preparation for a telemedicine visit by the patient.

FIG. 1 is a block diagram of a system 100 for capturing a user constructed map of a bodily region of interest for remote telemedicine navigation according to one or more embodiments of the present invention. A healthcare-professional 101 submits a request for a scan of a specific bodily region, such as arm, torso, heart, foot, knee, hip, shoulder, etc. from a user 107. The healthcare-professional 101 submits the request to a cloud-server 104 via a communication device 102. The cloud-server 104 includes one or more server computers (not shown in FIG. 1). The request can include an identity of the user 107, identity of the bodily region to be acquired, a viewing-sequence for the captured data, and a quality threshold for the captured data.

The identification of the user 107 can include a unique code that is associated with the user, a name, a birthdate, and other such identification information or a combination thereof. The identity of the bodily region can include a name, an identification number, an image, and/or other such information or a combination thereof. The viewing-sequence for the captured data can determine how the captured data is used to construct a rendering model of the bodily region when displaying the captured data to the healthcare-professional 101. The viewing-sequence can vary from one healthcare-professional to another, based on his/her practice, level of experience, knowledge of the bodily region, familiarity with the patient, previous diagnoses, personal skills and capabilities, and overall preference regarding the viewing-sequence. For example, a first healthcare-professional when examining an ankle may start from the front of the ankle and work his/her way around, while a second healthcare-professional may start from the back of the ankle and work his/her way around to the front. It is understood that other variations are possible, including the assembling of a model in such a way that the viewing-sequence can be altered by the healthcare-professional during the examination, and that ankle is just an example of a bodily region with such a variation.

The cloud-server 104 forwards the request to a user-device 106. The user-device 106 is a computing device, such as a laptop computer, a tablet computer, a phone, a desktop computer, or any other such computing device. The user-device 106 facilitates the user 107 to use a capture-device 108 to scan and capture the data for the bodily region that is specified in the request. The capture-device 108 can be a body scanning apparatus such as an ultrasound machine, an X-ray machine, or any other such body scanning apparatus. In one or more embodiments of the present invention, the capture-device 108 provides a haptic feedback to the user 107 during the data capture. The user-device 106 facilitates the use to capture the data for the bodily region by providing a visual feedback via a user-interface. The visual feedback includes a guide for the user to move him/herself or the capture-device 108 to capture specific data from the bodily region. In addition, the visual feedback includes an indicator of the quality of the data being captured. The visual feedback also includes guidance regarding how to improve the quality of the data to meet the quality threshold specified by the healthcare-professional 101.

In one or more embodiments of the present invention, the cloud-server 104 facilitates the user 107 to use the capture-device 108 to scan the specified bodily-region. For example, the cloud-server 104 executes an application that has a user-interface that is displayed on the user-device 106. The cloud-server 104 provides the visual feedback to the user 107, as described herein.

The captured data is compiled into a model that can be transferred to the healthcare-professional 101 and rendered via the communication device 102. The compilation of the model is performed based on the viewing-sequence specified by the healthcare-professional 101. It should be noted that the data may be captured in a different sequence by the user than the viewing-sequence, which is used to compile the model that is rendered to the health-care professional 101.

FIG. 1 depicts two users 107 with their respective user-devices 106 and capture-devices 108. It is understood that in other embodiments of the invention, the number of users 107 can be different. Further, each user 107 can use a different type of user-device 106, and/or a different type of capture-device 108. For example, a first user 107 may use a first type of capture-device 108 to acquire a tele-palpation for a swollen lymph node, while a second user 107 may use an imaging device to capture a bone-density scan of an arm. It is understood that above is just one example scenario, and that in other embodiments the specified bodily region for the scans, and/or the capture-devices 108 can be different.

Figure 2:
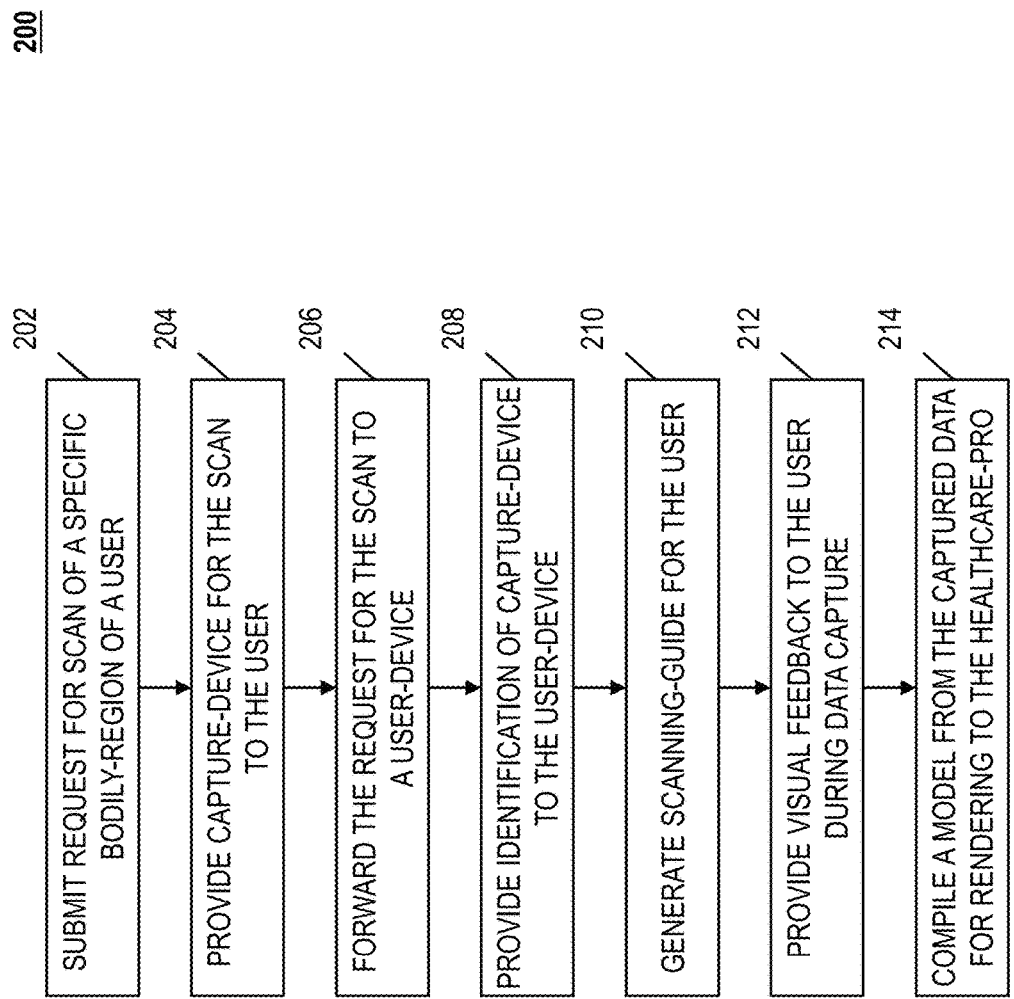
FIG. 2 is a flowchart of a method for capturing a user constructed map of a bodily region of interest for remote telemedicine navigation according to one or more embodiments of the present invention.

FIG. 2 depicts a flowchart of a method 200 for capturing a user constructed map of a bodily region of interest for remote telemedicine navigation according to one or more embodiments of the present invention. In the method 200, at block 202, the healthcare-professional 101 submits the request for capturing a specific bodily-region of the user 107. The request is submitted to the cloud-server 104.

In one or more embodiments of the present invention, the capture-device 108 can be readily available to the user 107, for example, a blood-pressure monitor, etc. However, in some cases, the capture-device 108 may not be readily available to the user 107, for example, a bone-density scanner, x-ray machine, etc. The cloud-server 104 has access to a list of capture-devices 108 to which the user 107 has access. For example, the user 107 has a profile that includes the list of the capture-devices 108 to which the user 107 has access. Accordingly, the cloud-server 104 determines whether the user 107 has access to the required capture-device 108 for the submitted request.

In the case that the user 107 does not have access, in one or more embodiments of the present invention, the cloud-server 104 facilitates providing the capture-device 108 to the user 107, at block 204. In one or more embodiments of the present invention, the cloud-server 104 determines a location that has the capture-device 108 for scanning the specified bodily-region. The cloud-server 104 has access to the user's 107 address, and/or present location, for example, via the user-device 106. The cloud-server 104 also has access to various locations where instances of the capture-device 108 are available. The cloud-server 104 can determine a list of the instances of the capture-devices 108 in the vicinity, for example, 25-miles, 10-miles, etc. of the user 107. The list of such available capture-devices 108 can be sent to the user 107, who can subsequently, make an appointment for using the capture-device 108 at the identified location. Alternatively, the cloud-server 104 sends a request to a third-party, such as an insurance provider, a clinic, a capture-device library, or any other such provider of the capture-device 108, to send the capture-device 108 to the user 107 at the address or location of the user 107. For example, the cloud-server 104 sends a request to the insurance provider of the user 107, the insurance provider known to the cloud-server 104 via the user's profile. In response, the insurance provider facilitates sending the capture-device 108 to the user 107. Alternatively, the cloud-sever 104 sends the location of the capture-device and library with authorization and instructions to the user to pick up the capture-device.

Further, in the method 200, at block 206, the cloud-server 104 forwards the request that is submitted by the healthcare-professional 101 to the user-device 106. Along with the request, in one or more embodiments of the present invention, the cloud-server 104 also sends to the user-device 106 an identification of the capture-device 108, at 208. The identification of the capture-device 108 can include a model number, a version number, and other such information that facilitates the user-device 106 to determine the characteristics of the capture-device 108 that the user 107 will be using to perform the scan. The user-device 106, based on the request from the healthcare-professional 101 and the identification of the capture-device 108, generates a scanning-guide for the user 107, at block 210.

When the user 107, uses the capture-device 108, in conjunction with the user-device 106, to scan and capture data for the bodily-region as requested by the healthcare-professional 101, the user-device 106 provides a visual feedback to the user 107 based on the scanning guide, at block 212. The visual feedback during the data capture ensures that the user 107 uses the capture-device 108 to cover the entire area of interest from the bodily region.

The visual feedback can include rendering portions of the bodily region as they are scanned in real-time on the user-device 106.

For example, consider that a user 107 has complained about swollen lymph node in his neck. In response, the healthcare-professional 101 requests a tele-palpation of the user's neck, jaw, and shoulders. The healthcare-professional 101 sends the request, which is forwarded to the user's smart phone (user-device 106). The user-device 106 further receives an identification of a diagnostician haptic interface (capture-device 108) for the tele-palpation. The capture-device 108 can be shipped to the user 107 by the insurance provider, or any other entity. Alternatively, the user 107 travels to a location where the capture-device 108 is available for his/her use.

To perform the scan, the user-device 106 parameterizes the construction of a template of the bodily region, in this case the neck region, for display to the user 107. In an embodiment of the present invention, as the user begins capturing the scan of the neck in this case, a model of the neck from both sides of the neck, from jawline to shoulder is rendered. Further, the visual feedback from the user-device 106 includes changes to the colors of one or more regions of the displayed model to indicate the quality and completeness of data collected from those regions.

The visual feedback can further include indication of a duration for which the user 107 has to hold the capture-device 108 in contact with, or in the vicinity of a portion of the bodily-region that is being scanned. The visual feedback can include a countdown, a progress-bar, or any other type of visual indicator to inform the user 107 to maintain a present position until the scanning of that portion is completed. An audible feedback can also be provided in conjunction in one or more embodiments of the present invention. Once the scan of a specific portion of the bodily region is completed, the user-device 106 can indicate to the user 107 to move to a next portion, if any.

Figure 3:
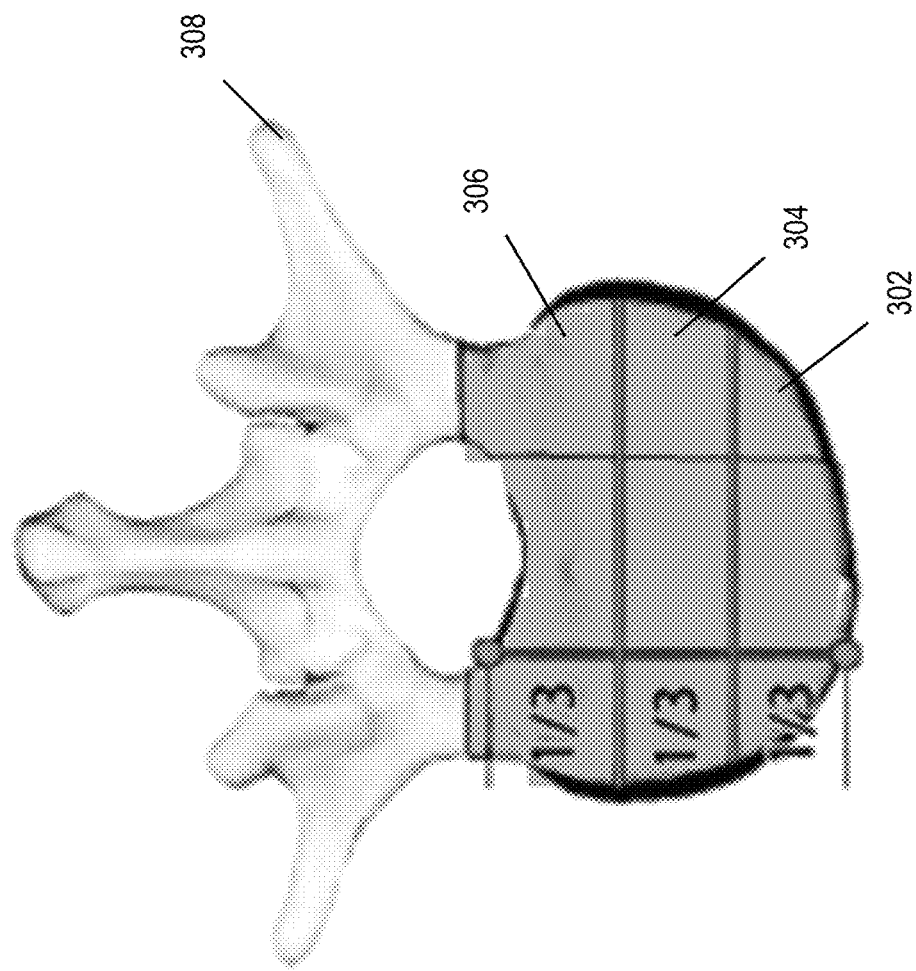
FIG. 3 is a depiction of a visual feedback for capturing a user constructed map of a bodily region of interest for remote telemedicine navigation according to one or more embodiments of the present invention.

FIG. 3 depicts an example of visual feedback provided to a user during a tomographic bone scan of a human vertebrae according to one or more embodiments of the present invention. Shown in FIG. 3 is a superior view that the healthcare-professional has requested. The visual feedback 300 shows a typical outline of the bodily-region to be scanned, in this case, the vertebrae, divided into four portions 302, 304, 306, 308; however, in other embodiments of the present invention, the bodily region can be divided into a different number of portions, for example, three, six etc. In the limit, the number of divisions may equal the number of pixels sampled by the capture-device, and thus the visual feedback 300 would be at the resolution of the capture-device or the visual rendering of the bodily-region. Note that the displayed outline of the bodily-region may be representative of an average human bodily-region, or the expected shape of the bodily-region given other specific information about the user; the outline may also be constructed and personalized based on previous measurements of the bodily region. The user 107 is informed to place the capture-device 108 close to, or in contact with each of the portions 302, 304, 306, 308. The user 107 can scan the bodily region in any sequence of the portions, for example 302-304-306-308, or 308-306-304-302, or any other order. As the capture-device 108 is close to particular portion, say the portion 302, the visual feedback 300 can highlight that portion 302, and further, indicate to the user 107 to maintain the present position of the capture-device 108 until that portion 302 is scanned with at least a predetermined quality.

In one or more embodiments of the present invention, the determining of the quality of the captured data can be performed by the user-device 106. Alternatively, or in addition, the cloud-server 104 determines the quality of the captured data. In this case, the captured data is first transmitted to the cloud-server 104. A result of the quality determination is sent to the user-device 106, which in turn provides the feedback 300 to the user 107.

The quality of captured data for the portion 302 can be determined based on multiple parameters, including, but not limited to resolution, contrast, noise-level, and other such parameters. If the specified quality parameters satisfy respective thresholds included in the request from the healthcare-professional 101, the portion 302 is deemed to be scanned. The visual feedback 300 indicates to the user 107 to move to one of the other portions 304, 306, 308. The above steps are repeated for the remaining portions until all of the portions 302, 304, 306, 308 are scanned to satisfy the quality threshold requirements. The scan of each portion 302, 304, 306, 308 is deemed completed, if the quality threshold(s) for that portion are satisfied. If the thresholds are not satisfied, the visual feedback 300 does not update to indicate that a portion is completed; rather, the visual feedback 300 indicates that the scanning of that portion is incomplete. The scanning of the bodily region is deemed completed once all of the portions (302, 304, 306, 308) are completed. In the example scenario shown in FIG. 3, the portions 302, 304, 306 have been scanned, and hence, those portions are highlighted, whereas, scanning of the portion 308 is yet to begin.

Referring to the flowchart in FIG. 2, once all of the portions 302, 304, 306, 308, in the bodily region are entirely scanned, a model for the bodily region is compiled, at block 214. In one or more embodiments of the present invention the captured data is transformed into a healthcare-professional-centric coordinate system for rendering to the healthcare-professional. For example, in the example scenario regarding capturing the tele-palpation, once a palpation map of the neck, is completed, the captured data is transformed for use in virtual palpation of the entire region for rendering to the healthcare-professional 101. In one or more embodiments of the present invention, the healthcare-professional-centric coordinate system is referenced in presenting the data to the healthcare-professional 101 based on healthcare-professional's own movements of an input device that is coupled with the communication device 102. The healthcare-professional's own movement of the input device is referenced in presenting the data to the user 107 during a subsequent telemedicine consultation.

The data that is captured by the capture-device 108 can include multiple images. The data can also include multiple point-clouds. In one or more embodiments of the present invention, the data can also include voxel data. Each portion (302, 304, 306, 308) of the bodily region can include any combination of the different types of data. The different types of data are stored in electronic format. The data can be stored in the user-device 106. The data can also be transferred and stored in the cloud-server 104.

In one or more embodiments of the present invention, the division of the bodily region into portions can facilitate the user 107 to take one or more breaks between the portions to be completed the entire scan of the bodily region 208. This can be particularly helpful for elder patients, or patients that may have some kind of disability that may prevent them from completing the entire scan in a single session. For example, after completing scans for the portions 302, 304, the user 107 can take a break, and upon returning complete the remaining portions 306, 308. It is understood that the sequence of scanning the portions and taking a break can vary in other embodiments of the present invention.

The compilation of the model can be performed by the user-device 106 or the cloud-server 104. The compilation is performed based on the viewing-sequence that is included in the request from the healthcare-professional 101.

In one or more embodiments of the present invention, wherein the user 107 is not the patient him/herself, but rather is a technician or any other such user acting as a proxy between the healthcare-professional and a patient, where the user 107 and collects the data of the patient so that the healthcare-professional 101 may observe patient body regions in advance of a subsequent appointment between the healthcare-professional 101 and the patient.

Figure 4:
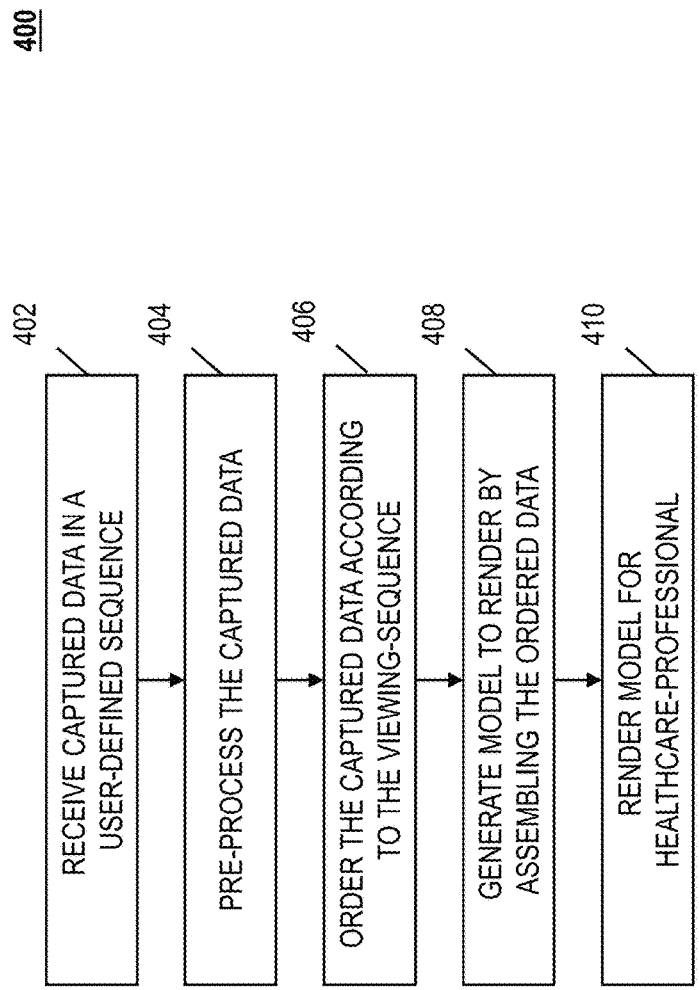
FIG. 4 is a flowchart of a method for compiling a user constructed map of a bodily region of interest for remote telemedicine navigation according to one or more embodiments of the present invention.

FIG. 4 depicts a flowchart for a method 400 of compiling a model for the healthcare-professional 101 from the data captured by the user 107 according to one or more embodiments of the present invention. The method 400 can be performed by the user-device 106, the cloud-server 104, or by the communication device 102. The method 400 includes receiving the data captured by the capture-device 108 in electronic format, and in a user-defined sequence, at block 402. The user-defined sequence is the sequence in which the user 107 captures the one or more portions of the bodily-region. The user-defined sequence can be different from the viewing-sequence that is provided by the healthcare-professional 101.

At block 404, the captured data is pre-processed. The pre-processing can include denoising, normalizing, aligning, registering, and other such operations that are performed to facilitate combining the separate data captures from the capture-device 108.

The pre-processed data is ordered using the viewing-sequence, at block 406. For example, the portions 302, 304, 306, 308 can be reordered as prescribed by the viewing-sequence. The viewing-sequence is the order in which the healthcare-professional 101 prefers to check the bodily region. For example, if the healthcare-professional 101 checks the bodily region in FIG. 3 in the order portions 308, 306, 304, 302, the data is assembled in that order to generate a model that is to be rendered to the healthcare-professional 101, at block 408.

At block 410, the rendering model is displayed at the communication device 102. Rendering the model can include an interactive rendering of the model of the bodily region. The healthcare-professional 101 can view and interact with the model via a user-interface of the communication device 102. The healthcare-professional 101 can accordingly study the bodily region of the user 107 remotely and in an asynchronous manner from the data capture to diagnose/analyze the condition of the bodily region. For example, in the above described example of the tele-palpation of the neck, the healthcare-professional 101 explores remotely at a later time the rendering of the neck as if he/she were palpating the neck in arbitrary orientations and sequences.

In one or more embodiments of the present invention, the healthcare-professional 101 can setup an appointment with the user 107 (or the patient) to discuss the findings of the healthcare-professional 101. The subsequent appointment can be an in-person appointment, a telemedicine appointment, or any other type of appointment to discuss the findings.

It should be noted that throughout the methods described herein, the data that is captured by one device can be transferred to another apparatus using a wired or a wireless connection. For example, the user-device 106 can have a wired connection with the capture-device 108 to facilitate transferring the captured data to the user-device 106. The user-device 106 can have a wireless connection with the cloud-server 104 to facilitate transfer of data. Further, the cloud-server 104 can use a wireless another connection with the communication device 102 to transfer data. The wireless data transfer can be performed using the Internet using one or more known communication protocols such as Ethernet. The wired data transfer can also be performed over the Internet using known communication protocols such as Ethernet. In addition, the wired transfer, for example between the capture-device 108 and the user-device 106 can be performed using proprietary communication protocol supported by the capture-device 108. It is understood that any other combination of wired and wireless data transfer can be used by the system 100.

In one or more embodiments of the present invention, the data that is transferred between the one or more devices in the system 100 is encrypted and decrypted using one or more data security techniques, such as public/private key encryption.

One or more embodiments of the present invention facilitate directing a user, without words, to record data from a bodily region for subsequent rendering in a healthcare-professional-centric coordinate and viewing system. The user views a representation of the bodily region in schematic form on a display to receive visual feedback in this regard. The location of user's movement of the capture-device 108 over the bodily region is monitored and captured as part of the data captured for the bodily region. In addition, the capture-device 108 captures images, point clouds, voxels, and other types of data that facilitate the healthcare-professional 101 to analyze the anatomical structures of the bodily region. For example, the capture device can capture images of bones, tissue matter, skin, blood vessels, or any other anatomical structure from the bodily region. In some embodiments, the location of the user's 107 movement of the capture-device 108 is recorded by an associated camera or other location determining device (not shown) at some location and orientation. The device is separate from the capture-device 108 and is able to detect the location of the capture-device 108, for example, using photogrammetry.

The visual feedback modulates colors of one or more portions of the bodily region that is being scanned in the schematic representation. The color modulation depicts whether a portion has been successfully captured by the user 107, and whether the quality of the captured data satisfies one or more quality thresholds for the scan. The collected data is assembled into a rendering and transferred to the healthcare-professional 101. Other forms of visual feedback modulation are possible, including contrast, brilliance, brightness, sharpness, texture rendering, distance cues, distortion, or skew. In some embodiments, a visual feedback can also include the removal of color, texture, or other renderings along the outline of the bodily region. For example, to make the scanning more entertaining for a child, the bodily region may be wrapped in gift-wrap patterns, which are then removed as the scan progresses. While an "outline" herein refers to the contours and edges of the divisions or boundaries of the visual representation of the bodily region, in some embodiments of the invention, "outline" can also refer to the 2D surface of a 3D object, or the 3D volume of a scanned bodily region during a particular phase of a periodic signal (for example a heartbeat). A topological surface in any dimension is also an outline in one or more embodiments of the invention.

Figure 5:
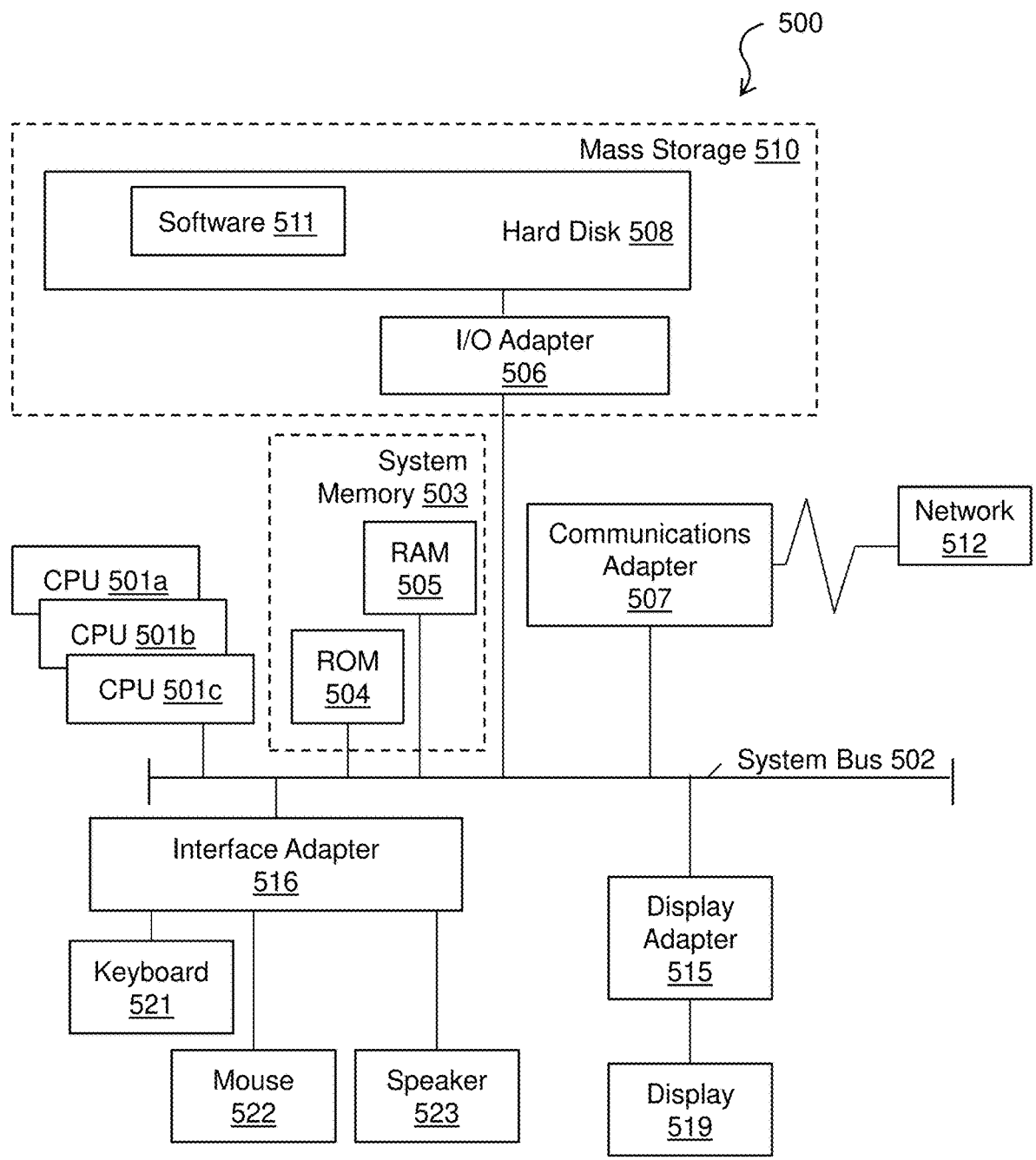
FIG. 5 depicts a computer system that implements one or more embodiments of the present invention.

Turning now to FIG. 5, a computer system 500 is generally shown in accordance with an embodiment. The computer system 500 can be used as any of the devices in the system 100, such as the user-device 106, the communication device 102, the cloud-server 104, the capture-device 108, or any other devices. The computer system 500 can be an electronic, computer framework comprising and/or employing any number and combination of computing devices and networks utilizing various communication technologies, as described herein. The computer system 500 can be easily scalable, extensible, and modular, with the ability to change to different services or reconfigure some features independently of others. The computer system 500 may be, for example, a server, desktop computer, laptop computer, tablet computer, or smartphone. In some examples, computer system 500 may be a cloud computing node. Computer system 500 may be described in the general context of computer system executable instructions, such as program modules, being executed by a computer system. Generally, program modules may include routines, programs, objects, components, logic, data structures, and so on that perform particular tasks or implement particular abstract data types. Computer system 500 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, the computer system 500 has one or more central processing units (CPU(s)) 501*a*, 501*b*, 501*c*, etc. (collectively or generically referred to as processor(s) 501). The processors 501 can be a single-core processor, multi-core processor, computing cluster, or any number of other configurations. The processors 501, also referred to as processing circuits, are coupled via a system bus 502 to a system memory 503 and various other components. The system memory 503 can include a read only memory (ROM) 504 and a random access memory (RAM) 505. The ROM 504 is coupled to the system bus 502 and may include a basic input/output system (BIOS), which controls certain basic functions of the computer system 500. The RAM is read-write memory coupled to the system bus 502 for use by the processors 501. The system memory 503 provides temporary memory space for operations of said instructions during operation. The system memory 503 can include random access memory (RAM), read only memory, flash memory, or any other suitable memory systems.

The computer system 500 comprises an input/output (I/O) adapter 506 and a communications adapter 507 coupled to the system bus 502. The I/O adapter 506 may be a small computer system interface (SCSI) adapter that communicates with a hard disk 508 and/or any other similar component. The I/O adapter 506 and the hard disk 508 are collectively referred to herein as a mass storage 510.

Software 511 for execution on the computer system 500 may be stored in the mass storage 510. The mass storage 510 is an example of a tangible storage medium readable by the processors 501, where the software 511 is stored as instructions for execution by the processors 501 to cause the computer system 500 to operate, such as is described herein below with respect to the various Figures. Examples of computer program product and the execution of such instruction is discussed herein in more detail. The communications adapter 507 interconnects the system bus 502 with a network 512, which may be an outside network, enabling the computer system 500 to communicate with other such systems. In one embodiment, a portion of the system memory 503 and the mass storage 510 collectively store an operating system, which may be any appropriate operating system, such as the z/OS or AIX operating system from IBM Corporation, to coordinate the functions of the various components shown in FIG. 5.

Additional input/output devices are shown as connected to the system bus 502 via a display adapter 515 and an interface adapter 516 and. In one embodiment, the adapters 506, 507, 515, and 516 may be connected to one or more I/O buses that are connected to the system bus 502 via an intermediate bus bridge (not shown). A display 519 (e.g., a screen or a display monitor) is connected to the system bus 502 by a display adapter 515, which may include a graphics controller to improve the performance of graphics intensive applications and a video controller. A keyboard 521, a mouse 522, a speaker 523, etc. can be interconnected to the system bus 502 via the interface adapter 516, which may include, for example, a Super I/O chip integrating multiple device adapters into a single integrated circuit. Suitable I/O buses for connecting peripheral devices such as hard disk controllers, network adapters, and graphics adapters typically include common protocols, such as the Peripheral Component Interconnect (PCI). Thus, as configured in FIG. 5, the computer system 500 includes processing capability in the form of the processors 501, and, storage capability including the system memory 503 and the mass storage 510, input means such as the keyboard 521 and the mouse 522, and output capability including the speaker 523 and the display 519.

In some embodiments, the communications adapter 507 can transmit data using any suitable interface or protocol, such as the internet small computer system interface, among others. The network 512 may be a cellular network, a radio network, a wide area network (WAN), a local area network (LAN), or the Internet, among others. An external computing device may connect to the computer system 500 through the network 512. In some examples, an external computing device may be an external webserver or a cloud computing node.

It is to be understood that the block diagram of FIG. 5 is not intended to indicate that the computer system 500 is to include all of the components shown in FIG. 5. Rather, the computer system 500 can include any appropriate fewer or additional components not illustrated in FIG. 5 (e.g., additional memory components, embedded controllers, modules, additional network interfaces, etc.). Further, the embodiments described herein with respect to computer system 500 may be implemented with any appropriate logic, wherein the logic, as referred to herein, can include any suitable hardware (e.g., a processor, an embedded controller, or an application specific integrated circuit, among others), software (e.g., an application, among others), firmware, or any suitable combination of hardware, software, and firmware, in various embodiments.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
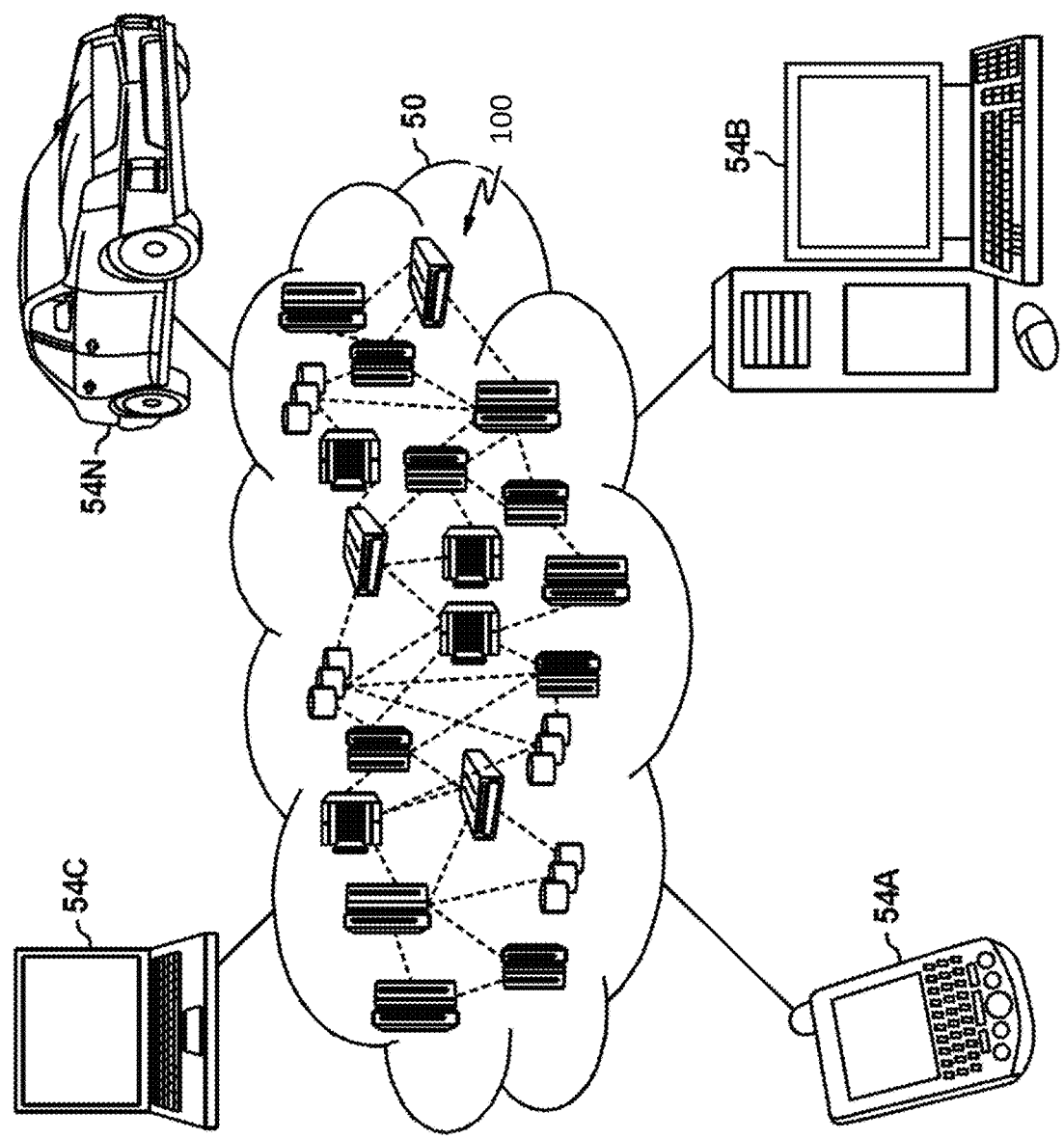
FIG. 6 depicts a cloud computing environment according to one or more embodiments of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
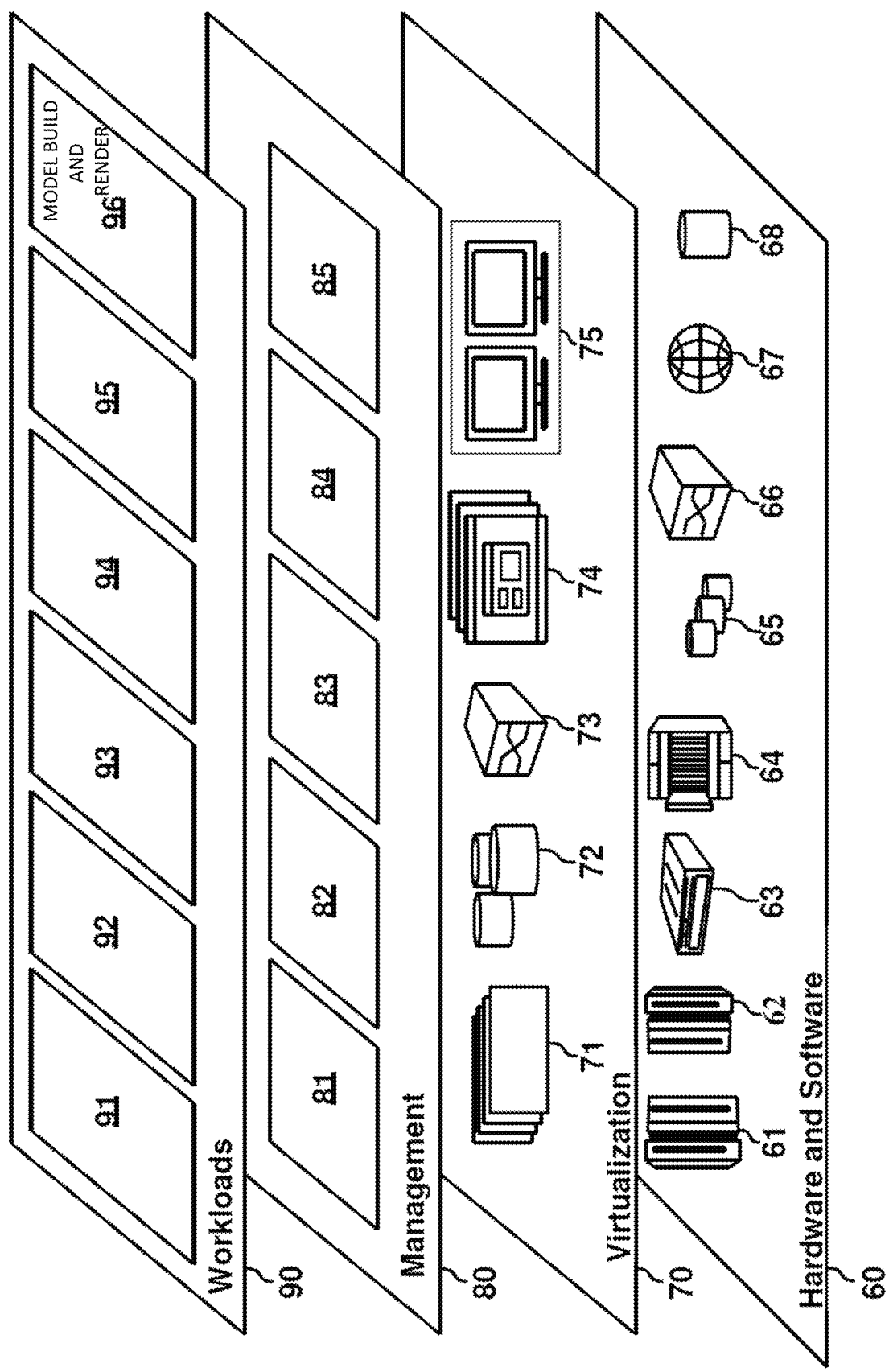
FIG. 7 depicts abstraction model layers according to one or more embodiments of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and computer vision 96. The computer vision 96 can include capturing the bodily-region point cloud and images, generating a model, rendering the model, and interaction with the model, among other functions required for implementing the one or more features described herein.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN)

or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method for capturing a user constructed map of bodily region of interest for remote telemedicine navigation, the computer-implemented method comprising:
   receiving, by a user-device, a request for capturing data for constructing a model of the bodily region using a designated capture-device;
   generating, by the user-device, a visual feedback for capturing the data, wherein generating the visual feedback comprises:
      displaying a representation of the bodily region;
      modulating, in response to the capture-device scanning the bodily region, the representation with a first indicator that indicates a duration to maintain a position of the capture-device; and
      further modulating, in response to completion of scanning the bodily region, the representation with a second indicator that indicates completion of the scan; and
   constructing, by the user-device, the model of the bodily region using data that is acquired by the capture-device by scanning the bodily region.

2. The method of claim 1, wherein modulating the representation comprises changing at least one from a group of parameters comprising color, contrast, brilliance, brightness, sharpness, texture rendering, distance cues, distortion, and skew of the representation.

3. The method of claim 1 further comprises transmitting the constructed model of the bodily region for visualization and interaction by a healthcare-professional.

4. The method of claim 3 further comprises encrypting the model of the bodily region prior to the transmitting.

5. The method of claim 1, wherein the representation of the bodily region is divided into a plurality of portions, and each portion is captured separately by the capture-device.

6. The method of claim 1, wherein determining completion of the scan by the capture-device comprises comparing one or more quality parameters of the scan with respective quality thresholds.

7. The method of claim 6, wherein the quality thresholds are prescribed as part of the request for capturing data.

8. A system comprising:
   a memory having computer readable instructions; and
   one or more processors for executing the computer readable instructions, the computer readable instructions controlling the one or more processors to perform operations for capturing user constructed map of bodily region of interest for remote telemedicine navigation, the operations comprising:
      receiving a request for capturing data for constructing a model of the bodily region using a designated capture-device;
      generating a visual feedback for capturing the data, wherein generating the visual feedback comprises:
         displaying a representation of the bodily region;
         modulating, in response to the capture-device scanning the bodily region, the representation with a first indicator that indicates a duration to maintain a position of the capture-device; and further modulating, in response to completion of scanning the bodily region, the representation with a second indicator that indicates completion of the scan; and constructing the model of the bodily region using data that is acquired by the capture-device by scanning the bodily region.

9. The system of claim 8, wherein modulating the representation comprises changing at least one from a group of parameters comprising color, contrast, brilliance, brightness, sharpness, texture rendering, distance cues, distortion, and skew of the representation.

10. The system of claim 8, wherein the one or more processors further perform operations comprising transmitting the constructed model of the bodily region for visualization and interaction by a healthcare-professional.

11. The system of claim 10, wherein the one or more processors further perform operations comprising encrypting the model of the bodily region prior to the transmitting.

12. The system of claim 8, wherein the representation of the bodily region is divided into a plurality of portions, and each portion is captured separately by the capture-device.

13. The system of claim 8, wherein determining completion of the scan by the capture-device comprises comparing one or more quality parameters of the scan with respective quality thresholds.

14. The system of claim 13, wherein the quality thresholds are prescribed as part of the request for capturing data.

15. A computer program product comprising a computer readable storage medium having program instructions embodied therewith, the program instructions executable by one or more processors to cause the one or more processors to perform operations for capturing user constructed map of bodily region of interest for remote telemedicine navigation, the operations comprising:

receiving a request for capturing data for constructing a model of the bodily region using a designated capture-device;

generating a visual feedback for capturing the data, wherein generating the visual feedback comprises:
displaying a representation of the bodily region;
modulating, in response to the capture-device scanning the bodily region, the representation with a first indicator that indicates a duration to maintain a position of the capture-device; and
further modulating, in response to completion of scanning the bodily region, the representation with a second indicator that indicates completion of the scan; and constructing the model of the bodily region using data that is acquired by the capture-device by scanning the bodily region.

16. The computer program product of claim 15, wherein modulating the representation comprises changing at least one from a group of parameters comprising color, contrast, brilliance, brightness, sharpness, texture rendering, distance cues, distortion, and skew of the representation.

17. The computer program product of claim 15, wherein the one or more processors further perform operations comprising transmitting the constructed model of the bodily region for visualization and interaction by a healthcare-professional.

18. The computer program product of claim 17, wherein the one or more processors further perform operations comprising encrypting the model of the bodily region prior to the transmitting.

19. The computer program product of claim 15, wherein determining completion of the scan by the capture-device comprises comparing one or more quality parameters of the scan with respective quality thresholds.

20. The computer program product of claim 19, wherein the quality thresholds are prescribed as part of the request for capturing data.

21. A method for capturing user constructed map of bodily region of interest for remote telemedicine navigation, the computer-implemented method comprising:

receiving, by a cloud-server, a request for capturing data for constructing a model of the bodily region of an identified user;

determining, by the cloud-server, a designated capture-device to be used by the identified user to capture the data for constructing the model;

transmitting, by the cloud-server, the request to a user-device associated with the user along with an identification of the designated capture-device;

providing, at runtime, by the cloud-server, a visual feedback for capturing the data, wherein generating the visual feedback comprises:
causing the user-device to display a representation of the bodily region;
modulating, in response to the capture-device scanning the bodily region, the representation with a first indicator that indicates a duration to maintain a position of the capture-device; and
further modulating, in response to completion of scanning the bodily region, the representation with a second indicator that indicates completion of the scan;

receiving, by the cloud-server, the data that is acquired by the capture-device; and constructing, by the cloud-server, the model of the bodily region using the data that is acquired by the capture-device by scanning the bodily region.

22. The method of claim 21 further comprises transmitting the constructed model of the bodily region for visualization and interaction by a healthcare-professional.

23. A system comprising:
a memory having computer readable instructions; and
one or more processors for executing the computer readable instructions, the computer readable instructions controlling the one or more processors to perform operations for capturing user constructed map of bodily region of interest for remote telemedicine navigation, the operations comprising:

receiving a request for capturing data for constructing a model of the bodily region of an identified user;

determining a designated capture-device to be used by the identified user to capture the data for constructing the model;

transmitting the request to a user-device associated with the user along with an identification of the designated capture-device;

providing, at runtime, a visual feedback for capturing the data, wherein generating the visual feedback comprises:
causing the user-device to display a representation of the bodily region;
modulating, in response to the capture-device scanning the bodily region, the representation with a first indicator that indicates a duration to maintain a position of the capture-device; and further modulating, in response to completion of scanning the bodily region, the representation with a second indicator that indicates completion of the scan;

receiving the data that is acquired by the capture-device; and constructing the model of the bodily region using the data that is acquired by the capture-device by scanning the bodily region.

24. The system of claim 23, wherein modulating the representation comprises changing at least one from a group of parameters comprising color, contrast, brilliance, brightness, sharpness, texture rendering, distance cues, distortion, and skew of the representation.

25. The system of claim 23, wherein the operations further comprise transmitting the constructed model of the bodily region for visualization and interaction by a healthcare-professional.

* * * * *